United States Patent [19]

Nappholz

[11] Patent Number: 5,441,523
[45] Date of Patent: Aug. 15, 1995

[54] FORCED ATRIOVENTRICULAR SYNCHRONY DUAL CHAMBER PACEMAKER

[75] Inventor: Tibor A. Nappholz, Englewood, Colo.

[73] Assignee: Telectronics Pacing Systems, Inc., Englewood, Colo.

[21] Appl. No.: 226,654

[22] Filed: Apr. 12, 1994

[51] Int. Cl.$^6$ ............................................. A61N 1/362
[52] U.S. Cl. ................................................... 607/14
[58] Field of Search ...................................... 607/9, 14

[56] References Cited

U.S. PATENT DOCUMENTS 4,702,253 10/1987 Nappholz et al. .
4,766,901 8/1988 Callaghan .
4,901,725 2/1990 Nappholz et al. .
5,085,215 2/1992 Nappholz et al. .
5,201,808 4/1993 Steinhaus et al. .

Primary Examiner—William E. Kamm
Assistant Examiner—Scott M. Getzow
Attorney, Agent, or Firm—Gottlieb, Rackman & Reisman

[57] ABSTRACT

A dual chamber cardiac pacemaker is adapted to operate in a forced synchrony pacing mode. The pacemaker senses atrial heartbeats and determines whether the rate of sensed atrial heartbeats is pathological or physiological. For physiological atrial heartbeat rates, the pacemaker functions in an AV synchronous pacing mode. For pathological atrial rates, atrial heartbeats occur too frequently for safe AV synchronous pacing so the heart is paced in the forced synchrony mode. In the forced synchrony mode, the pacemaker, upon sensing a natural atrial heartbeat, waits a predetermined atrial protection interval, paces the atria with an atrial stimulation pulse, waits a physiologically appropriate AV delay interval, and then delivers a ventricular pacing pulse at a time which maintains a stable ventricular rate.

40 Claims, 14 Drawing Sheets

FORCED ATRIOVENTRICULAR SYNCHRONY DUAL CHAMBER PACEMAKER

FIELD OF THE INVENTION

This invention relates to dual chamber pacemakers, and more particularly to a mode of operation in the presence of high intrinsic heart rates.

BACKGROUND OF THE INVENTION

The primary function of a pacemaker (cardiac pulse generator) is to sense for intrinsic (natural) events, that is, P-waves and R-waves, and if such are absent to provide stimulation or pacing pulses in either or both the atrium and the ventricle.

A dual chamber pacemaker stimulates a patient's heart in the most physiologically efficient manner when it provides atrioventricular [AV] synchrony. This means that each atrial contraction [P-wave] is followed, after an appropriate AV delay, by a ventricular contraction [R-wave], which is the sequence exhibited by a healthy heart.

Some patients, however, have not only slower than normal heart rates (bradycardia), but also faster than normal heart rates (tachycardia). Atrial tachycardias can be either physiological or pathological. Physiological atrial tachycardia denominates a fast sinus rate (rhythm) wherein the atrium is paced by the sinus node, and is the body's normal response to exercise. Pathological atrial tachycardia is an abnormal rhythm caused by a disease state. A dual chamber pacemaker should react appropriately to bradycardia, and physiological and pathological tachycardias.

In a dual chamber pacemaker, the rate of ventricular pacing pulses [V-pace] which are provided in the absence of sensed intrinsic ventricular activity [V-sense] is determined by the atrial channel. The atrial channel may either sense a P-wave [A-sense] or, in the absence of an A-sense, provide a pacing pulse [A-pace]. When the atrial channel senses a P-wave, the ventricular channel follows, one for one, providing a pacing pulse [V-pace] in the absence of a V-sense. This provides the intended therapy of increased hemodynamic output with increased sinoatrial rate.

However, the dual chamber pacemaker must cope with atrial tachycardias, and the mechanism to do this is the "programmed maximum rate." This maximum rate is usually the upper rate limit both (i) when the ventricular channel is tracking (or following) A-senses in the atrial channel, and (ii) when in the case of a sensor driven, rate responsive pacemaker, the atrial channel is pacing, i.e., providing A-paces. A rate responsive pacemaker has an independent sensor which measures a physical or metabolic parameter. The sinus rate is combined with the sensor indicated rate to determine the atrial pacing rate. This provides increased hemodynamic output for a patient who has sinus node disease.

The behavior of a pacemaker when it reaches the programmed maximum rate is referred to as the "upper rate response". Conventional dual chamber pacemakers employ one or more of a variety of known upper rate responses. The three best known are (i) "block", (ii) "Wenckebach", and (iii) "fallback".

In "block", the pacemaker ignores every second, or third, etc. A-sense depending on the atrial rate, and a V-pace is omitted for each ignored A-sense.

In "Wenckebach", the pacemaker progressively prolongs the AV delay after each A-sense so that a constant ventricular rate is maintained, the maximum rate. There comes a time, depending on the programmed pacemaker intervals and the atrial rate, that an A-sense is ignored and the corresponding V-pace is omitted. This is, in effect, an intermittent "block" response and, as the atrial rate increases, a greater proportion of the A-senses are ignored. This results in a progressively higher degree of "block", resulting in large cardiac cycle-to-cycle variations in the ventricular rate and in intermittent A-V synchrony.

In "fallback", the pacemaker on detecting an atrial rate which exceeds a programmed "tachycardia detection rate", which may be equal to or greater than the maximum rate, progressively lengthens the VV cycle until a programmed lower ventricular rate is obtained. Once this lower rate is obtained, pacing in the VVI mode ensues until the atrial rate drops below the tachycardia rate. AV synchrony is lost for the duration of the "fallback" response.

In U.S. Pat. No. 5,085,215, issued Feb. 4, 1992, to T. A. Nappholz et al, for "Metabolic Demand Driven Rate-Responsive Pacemaker", there is shown a pacemaker which automatically selects either a DDDR or VVIR pacing mode based on an analysis of the patient's intrinsic atrial rate compared to the rate indicated by a metabolic sensor. This comparison provides a classification of such intrinsic atrial rate as either physiological or pathological. This upper atrial rate response, called automatic mode switching [for which AMS is a trademark of Telectronics Pacing Systems, Inc.] provides AV synchrony for normal sinoatrial rates from the minimum to the maximum rate in the DDDR mode, and provides a stable ventricular rate in the VVIR mode, but with the loss of AV synchrony, in the presence of atrial arrhythmias.

SUMMARY OF THE INVENTION

This invention provides a dual chamber pacemaker with an upper atrial rate response which provides AV synchrony and a stable ventricular rate. This result is obtained by ensuring that every ventricular event is preceded by an atrial event at an acceptable physiological interval. If there is no A-sense at the appropriate time, then an A-pace is provided. A minimum physiologically acceptable programmed time between two successive atrial events, which is called the atrial protection interval [for which API is a trademark of Telectronics Pacing Systems, Inc.] is required before AV delay timing begins.

The API precludes pacing the atrium during its relative refractory period, sometimes called the vulnerable period, when arrhythmias may be induced. After satisfying the API requirement, the pacemaker's AV delay is adjusted to maintain a stable VV interval. This upper rate response is called "forced synchrony" and provides a stable ventricular rate with AV synchrony, but at a loss of maintaining a stable AV delay. However, the AV delay is maintained within physiological limits.

The primary improvement of this invention over the limitations of conventional dual chamber pacemakers is the provision of some degree of AV synchrony for intrinsic atrial rates that are above the maximum allowable ventricular pacing rate, with the elimination of rate variations due to higher block in Wenckebach. Another improvement is that instances of pacemaker mediated tachycardia [PMT] are minimized because AV synchrony is maintained.

Conventional pacemakers which employ the automatic mode switching upper rate response may induce pacemaker mediated tachycardia after an atrial arrhythmia has been terminated, when switching from the VVI or VVIR mode to the DDD or DDDR mode. During the first cardiac cycle after the mode switch, the origin of the first A-sense is unknown. It could be either of atrial origin, i.e., a P-wave, or a retrograde P-wave caused by the previous V-pace. Also, with a Wenckebach response the AV delay is prolonged and thus the atrium has a longer period in which to repolarize and thereby provide a retrograde pathway for conduction, which may permit pacemaker mediated tachycardia. However, the forced synchrony function of the present invention inserts an A-pace after an A-sense, and thereby the retrograde pathway is made refractory so that a pacemaker mediated tachycardia cannot be induced by retrograde conduction.

A feature of this invention is the provision of a dual chamber pacemaker with a forced synchrony function which constantly monitors where in the cardiac cycle atrial events occur.

If the atrial event occurs within a time window called the "Alert", then it is considered to be a P-wave of sinoatrial origin and it is tracked. In this case, there is no forced synchrony operation.

If the atrial event occurs before the Alert window, then forced synchrony is provided. Forced synchrony maintains a stable VV interval with AV synchrony by providing an A-pace after the API if needed.

There are two categories of atrial events which may occur outside the Alert window:

(i) An atrial event occurring in API or PVARP such that the remainder of the VV interval is greater than the programmed maximum AV delay, which is usually 260 ms In this case, an API and an AV delay are calculated, and an A-pace is provided at the end of the API. This provides the hemodynamic benefit of AV synchrony. This also makes the atrium and the AV node refractory to preclude a PMT.

(ii) An event occurring at higher rates in the PVARP or API such that prolongation of the AV delay will meet the needs of stabilizing the rate.

The calculation of the remainder of the VV interval is a constant process and is performed by what is called the "ventricular cardiac cycle timer [VCCT]. Depending on the prevailing cardiac rhythm, it is determined from one of three sources:

(i) the "average atrial rate" [AAR] (usually over the last four cycles) in DDD and DDDR modes.
(ii) the sensor derived "metabolic indicated rate" [MIR] (e.g., minute volume) in VVIR mode.
(iii) the programmed minimum rate (in the absence of a sensor).

When switching between these sources, there is a gradual transition to avoid erratic ventricular rates.

Forced synchrony may be implemented in several ways, either by using a separate controller, or as a modified response of a conventional dual chamber pacemaker. The preferred embodiment disclosed herein modifies the API, the AV delay, and the Alert window, as required on a cycle-by-cycle basis.

BRIEF DESCRIPTION OF THE DRAWINGS

Further objects, features and advantages of the invention will become apparent upon consideration of the following description, taken in conjunction with the accompanying drawing, in which.

DETAILED DESCRIPTION OF THE INVENTION

Figure 1:
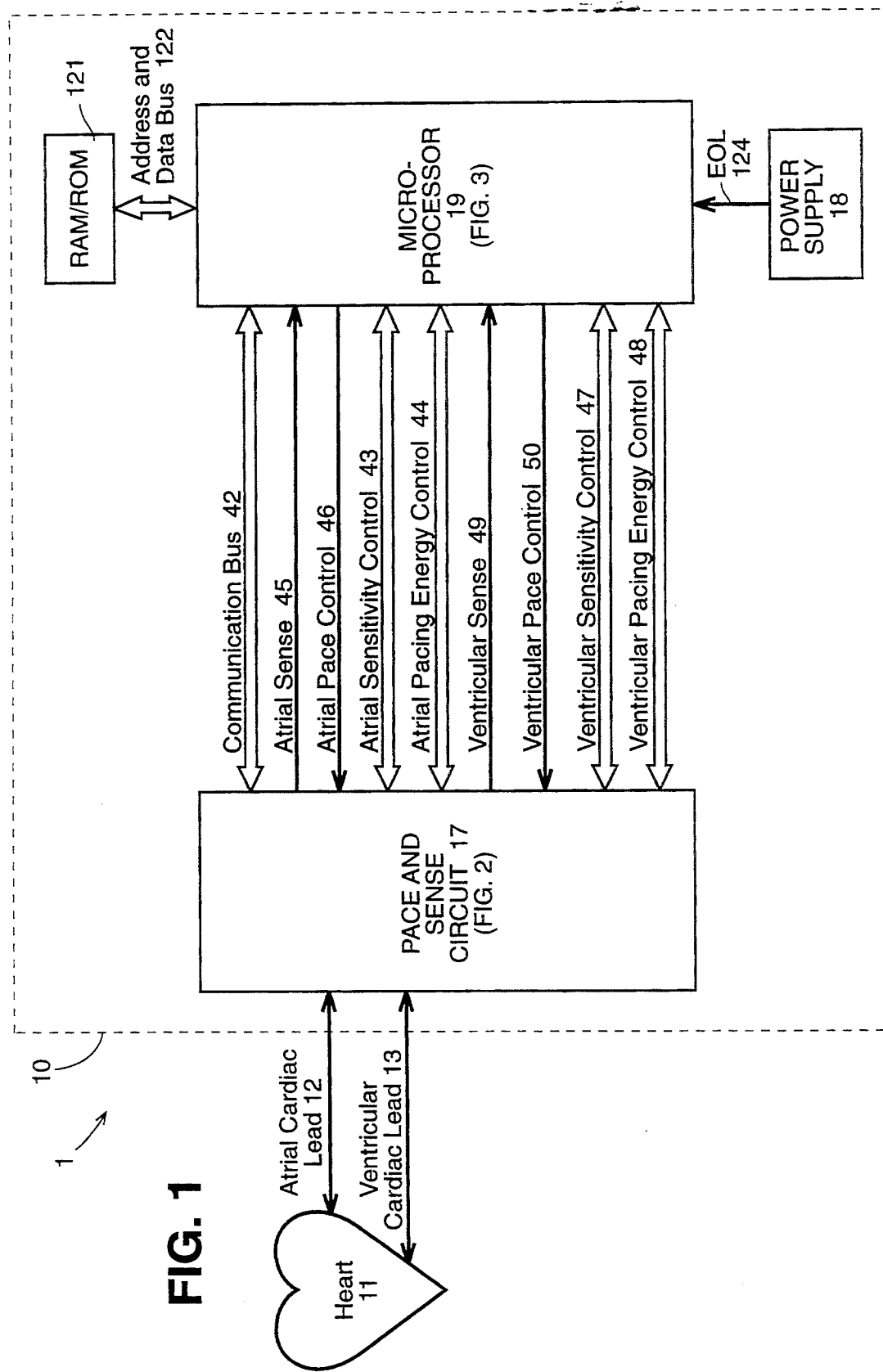
FIG. 1 is a block diagram of a rate-responsive, dual chamber pacemaker which embodies the subject invention.

FIG. 1 shows a block diagram of a pacemaker 1. The pacemaker 1 is designed to be implanted in a patient and includes a pulse generator 10 and appropriate leads for electrically connecting the pulse generator to a patient's heart 11. The pacemaker includes an atrial cardiac lead 12 extending to the atrium of the patient's heart for the administration of pacing therapy to the atrium, and a ventricular cardiac lead 13 extending to the ventricle of the patient's heart for the administration of pacing therapy to the ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
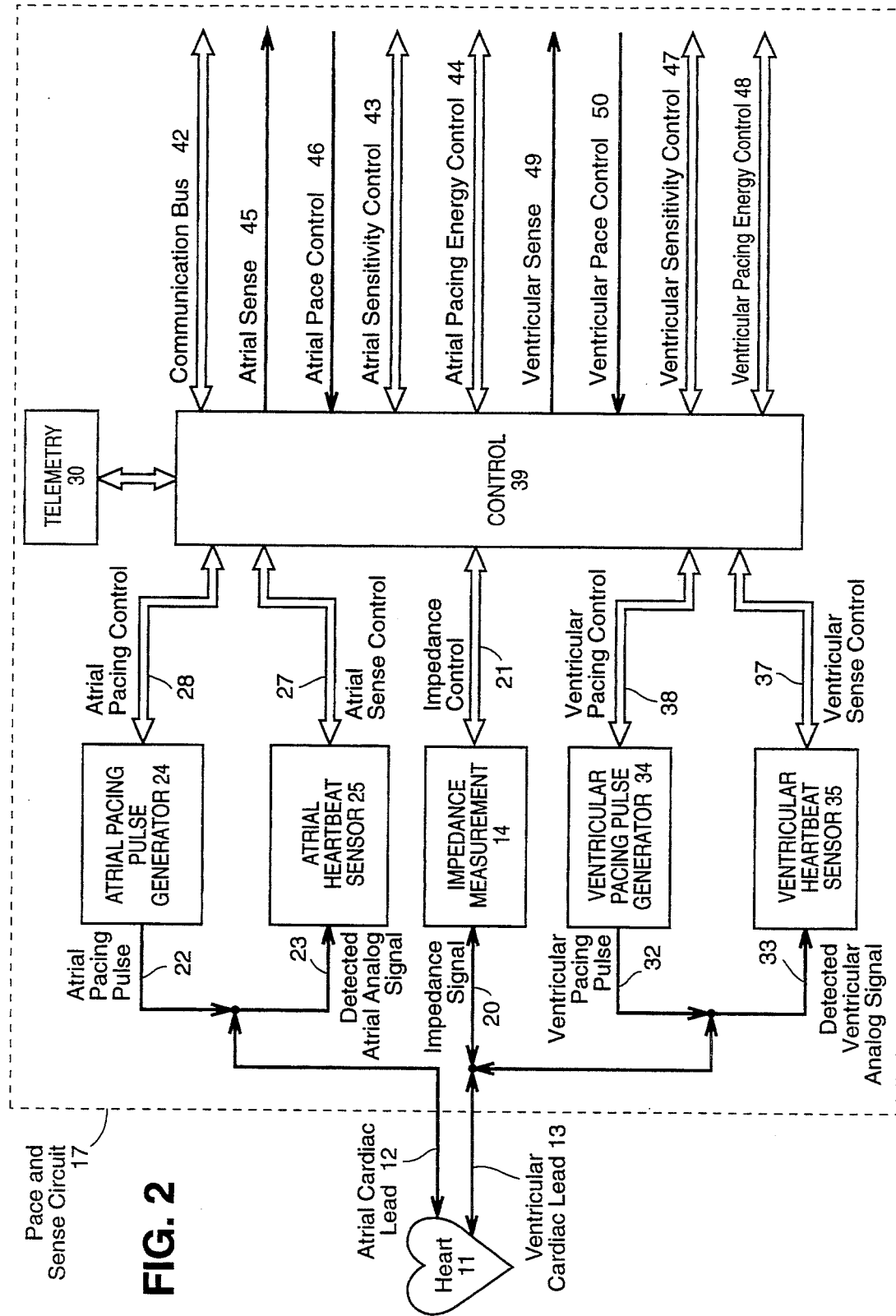
FIG. 2 is a block diagram of the pace and sense circuit 17 of FIG. 1.

FIG. 2 shows the pace and sense circuit 17 which includes circuitry for an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 includes an impedance measurement circuit 14 for measuring a physiological parameter indicative of the patient's metabolic demand. Also, the pace and sense circuit 17 includes a control block 39 which has an interface to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control 27 and an input ventricular sense control 37, respectively, from the control block 39 which determines the sensitivities of the sensor circuits. The sensitivity determines the minimum voltage deviation required at a sensing electrode for a sense to be registered, i.e., a depolarization signal to be recognized by the pacemaker.

The atrial pacing pulse generator circuit 24 receives from the control block 39, via an atrial pacing control bus 2,8, an atrial pace control input and an atrial pacing energy control input to generate an atrial pacing pulce 22 [A-pace] at appropriate times. Similarly, the ventricular pacing pulse generator circuit 34 receives from the control block 39, via a ventricular pacing control bus 38, a ventricular pace control input and a ventricular pacing energy control input to generate a ventricular pacing pulse [V-pace] 32. The atrial and ventricular pace control inputs determine the respective types of atrial and ventricular pacing that take place, while the atrial and ventricular pacing energy control inputs determine the respective magnitudes of the pulse energies.

The pacemaker 1 makes an impedance measurement when the microprocessor 19 sends a signal on the impedance control bus 21 to activate the impedance measurement circuit 14. The impedance measurement circuit 14 then applies a current to the ventricular cardiac lead 13 and measures a voltage resulting from the applied current to monitor the impedance. The current and voltage signals jointly are termed an impedance signal 20.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colorado, U.S.A.

Figure 3:
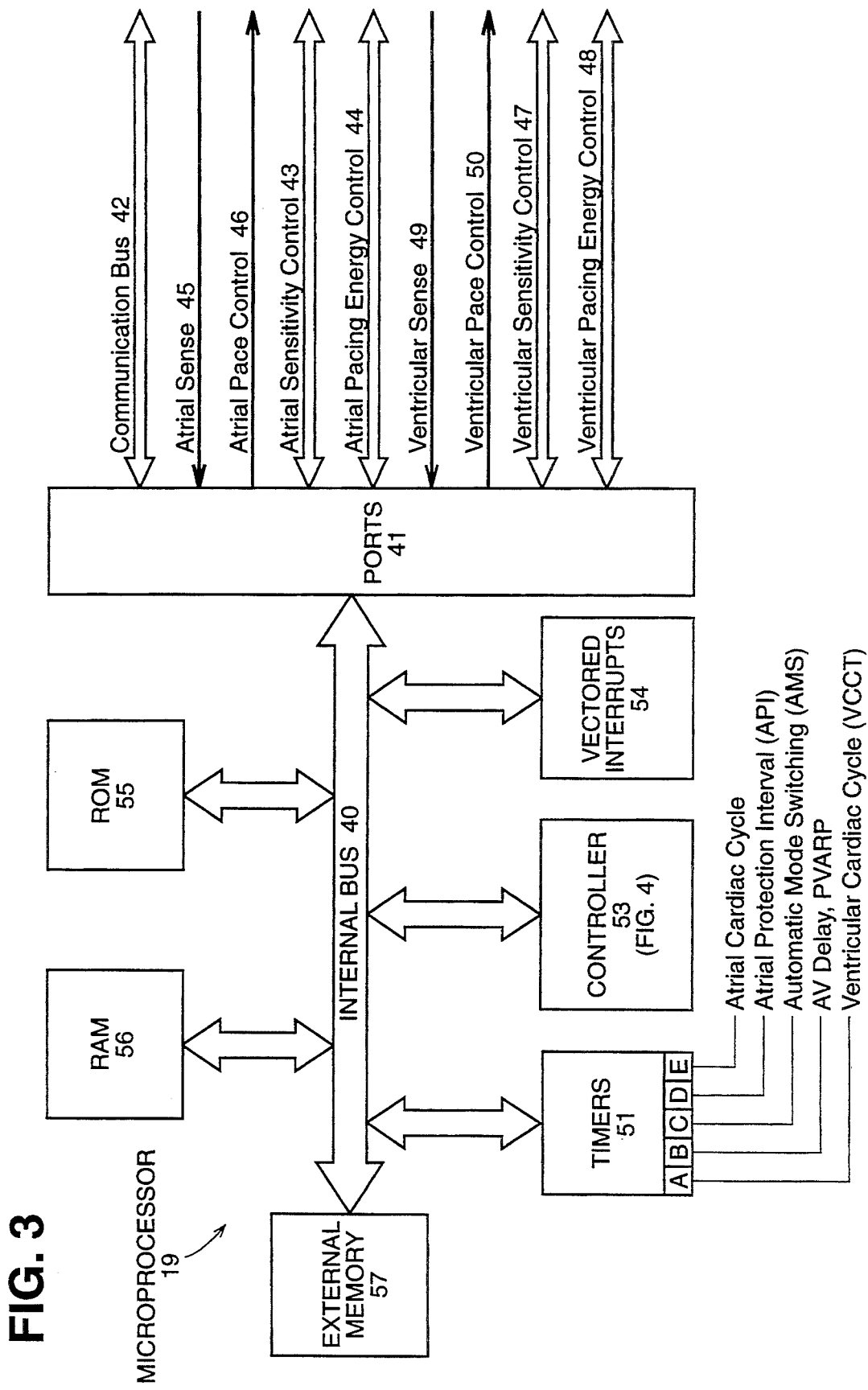
FIG. 3 is a block diagram of the microprocessor 19 of FIG. 1.

FIG. 3 shows the microprocessor 19 as comprising a timer circuit 51 which may include multiple individual 16-bit timer circuits, a controller 53, a vectored interrupts block 54, a ROM 55, a RAM 56, an external memory 57 and a ports block 41. These circuits mutually communicate using an internal communications bus 40.

In one embodiment of the invention, five timer circuits are required (for example, a ventricular cardiac cycle timer 51A an AV delay and PVARP timer 51B, an automatic mode switching (AMS) timer 51C, an atrial protection interval (API) timer 51D and an atrial cardiac cycle timer 51E). Thus, the timer 51 may include five individual circuits or may include one or more timer circuits with a single timer performing multiple function timing operations (such as timer 51B) under direction of software running on the controller 53. The RAM 56 acts as a scratchpad and active memory during execution of the programs stored in the ROM 55 and used by the microprocessor 19. These programs include system supervisory programs, detection algorithms for detecting and confirming arrhythmias, and programming for implementing the logic diagram of FIGS. 12, 13, 14 and 15, as well as storage programs for storing, in external memory 57, data concerning the functioning of the pulse generator 10 and the electrogram provided by the ventricular cardiac lead 13. The timers 51, and their associated control software, implement some timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communications bus 42 serves to provide signals indicative of such control to the microprocessor 19.

Appropriate telemetry commands will cause the telemetry circuit 30 to transmit data to the external programmer. Data stored is read out, by the microprocessor 19, on to the communications bus 42, through the control block 39 in the pace and sense circuit 17, and into the telemetry circuit 30 for transmission to the external programmer by a transmitter in the telemetry circuit 30.

The microprocessor 19 through its ports block 41 receives status and/or control inputs from the pace and sense circuit 17, such as the sense signals on the sense lines 45 and 49. It performs operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits.

The pacemaker 1 may employ a metabolic sensor to distinguish whether atrial heartbeats are occurring at a physiological :rate or a pathological rate. The pacemaker 1 responds to a physiological atrial rate by functioning in an AV synchronous pacing mode with pacing pulses in the ventricle delivered a predetermined interval following an atrial heartbeat. When the pacemaker 1 detects a pathological atrial rate, defined by an A-sense in API or PVARP, it responds by functioning in the forced synchrony mode of operation. A metabolic sensor system, which is suitable for operation in the present invention, may be made up of one or more known sensors either solely or in combination with other sensors, including but not limited to minute volume, ventricular depolarization gradient, QT-interval, oxygen saturation, Ph, central venous blood temperature, right ventricular pressure, stroke volume, systolic time intervals, respiration rate and ultrasonic or pressure monitoring of cardiac output. The pacemaker 1 of the present invention will function properly using any metabolic indicator rate system, so long as that system is able to reliably relate the sensed parameter to a metabolic demand pacing rate. U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential as a metabolic demand pacing rate indicator. U.S. Pat. No. 4,702,253 to T. Nappholz et al., issued Oct. 27, 1987, for "Metabolic-Demand Pacemaker and Method of Using the Same to Determine Minute Volume," U.S. Pat. No. 4,901,725, to T. Nappholz et al., issued Feb. 20, 1990 for "Minute Volume Rate-Responsive Pacemaker", and U.S. Pat. No. 5,201,808 to B. Steinhaus et al., issued Apr. 13, 1993 for "Minute Volume Rate-Responsive Pacemaker Employing Impedance Sensing On A Unipolar Lead", disclose rate-responsive pacers describing another metabolic demand pacing rate indicator, respiratory minute volume, as the rate control parameter. The above-mentioned patents are hereby incorporated by reference. The preferred embodiment of the invention employs an impedance sensor 14, shown in FIG. 2 which may perform the respiratory minute volume measurements of the Nappholz et al. patents.

Figure 4:
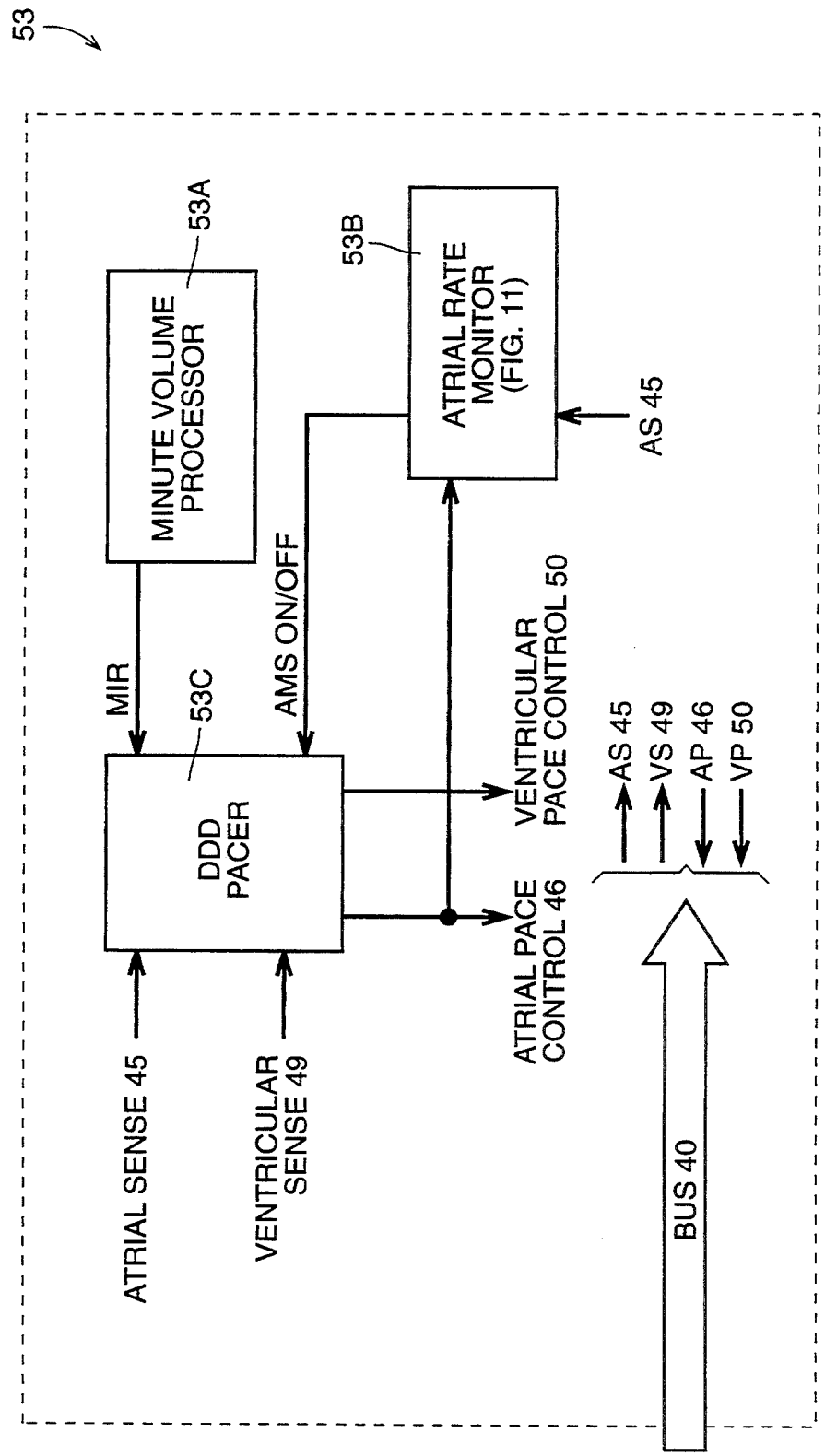
FIG. 4 is a functional block diagram of the controller 53 of FIG. 3.
Figure 11:
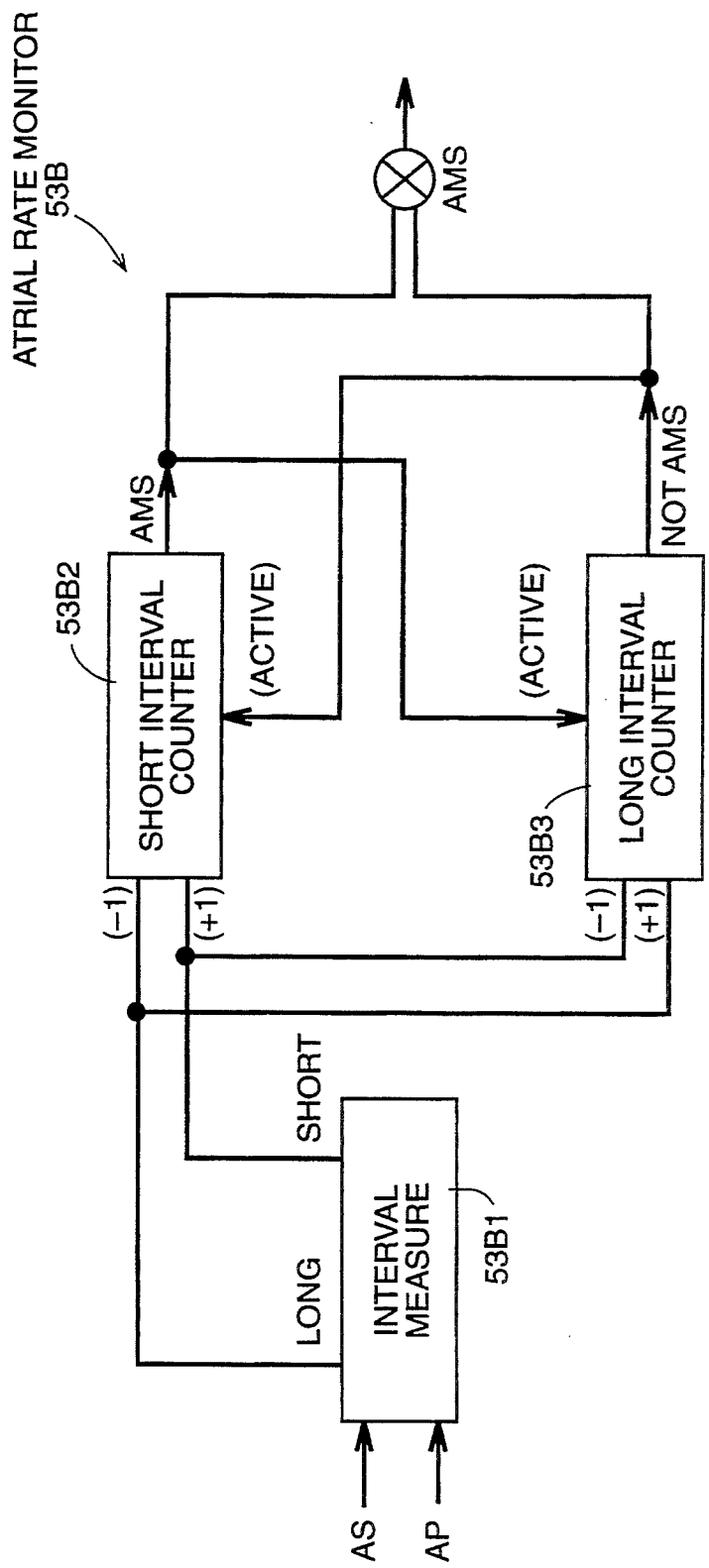
FIG. 11 is a functional block diagram of the atrial rate monitor 53B of the controller of FIG. 4.

FIG. 4 shows the functional block diagram of the controller 53 of FIG. 3. The minute volume processor 53A uses the data supplied via the internal bus 40 and the communication bus 42 from the impedance measurement block 14 to generate the Metabolic Indicated Rate Interval [MIR] which is used by the pacing and sensing system (shown symbolically as the "DDD pacer block 53C in FIG. 4) to determine the length of each of the intervals used in the timing cycle. The atrial rate monitor 53B, whose functional block diagram is depicted in FIG. 11, generates an AMS signal which will be described at length below. FIG. 4 depicts the signals which control several of the operations involved in the forced synchrony sequencing.

Figure 5:
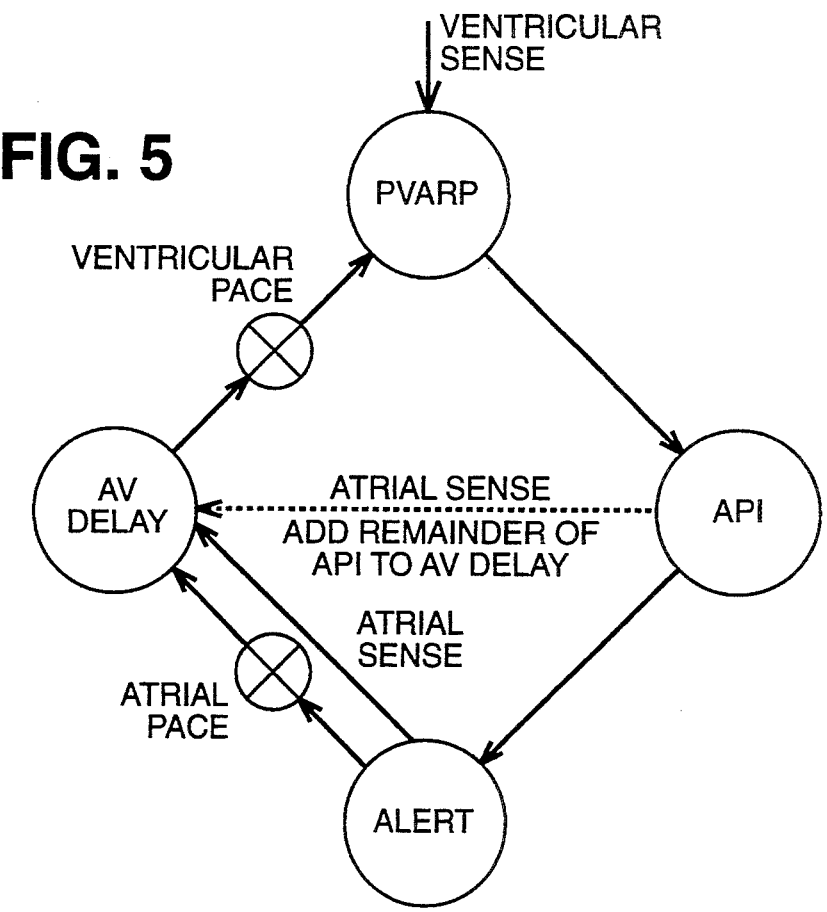
FIG. 5 is a state diagram that characterizes the operation of the pacemaker of FIG. 1.

The pacemaker state diagram is shown in FIG. 5. The PVARP is the Post Ventricular Atrial Refractory Period. An A-sense occurring during this interval is considered pathological, most likely due to a retrogradely conducted ventricular event, but is still used for A-sense counting (to determine the average atrial rate). A V-sense occurring at any time starts the PVARP.

Figure 6:
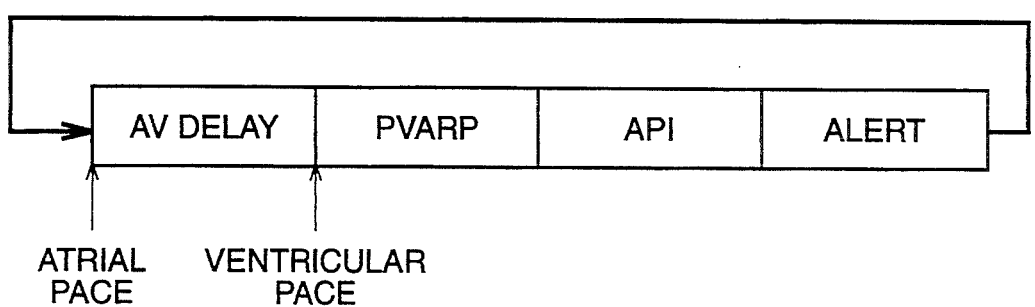
FIG. 6 is a line timing diagram that characterizes the operation of the pacemaker of FIG. 1.

The API is the Atrial Protection Interval and defines the minimum time between a pathological A-sense (i.e., in the PVARP) and the next A-pace. The API is intended to prevent an A-pace being provided during the vulnerable part of the atrial repolarization period, i.e., the relative refractory period during which arrhythmias may be induced. For example, the API may be controlled to ensure that the sum of the AV delay, the PVARP and the Alert interval is less than 70% of the VV rate interval indicated by the MIR. The API is set to meet limits dictated by the physiology of the heart. The API can be a specific window in the timing cycle as shown in FIG. 6. On the other hand, when the objective is to stabilize the ventricular rate, the API shifts and is timed from an event in PVARP.

The Alert is the interval during which A-senses are classified to be P-waves (i.e., of sinus origin) within the correct rate range. Such P-waves are tracked 1:1 by the ventricular channel. The Alert is the remainder of VV interval after the sum of the AV delay plus the PVARP plus the API.

The AV delay is intended to mimic the natural P-wave to R-wave interval and is the time between an A-sense (or A-pace) and a V-pace (in the absence of a V-sense).

There are four inputs, A-sense, V-sense, AMS and the MIR to the controller 53, which is the state sequencer. The A-sense and V-sense signals are processed by the atrial heartbeat sensor 25 and the ventricular heartbeat sensor 35 respectively, where refractory periods are used to blank the detected analog signals for predetermined periods. Any A-sense and V-sense signals extended to the controller 53 are considered to be cardiac in origin.

The following rules apply irrespective of the duration of the time intervals of each of the states. The A-pace and V-pace states do not have a time interval associated with them. The other four states have time intervals (which in some cases may be zero).

(i) In the absence of A-sense and V-sense signals, the states are timed sequentially and repeatedly—V-pace, PVARP, API, Alert, A-pace and AV delay.

(ii) If a V-sense occurs at any time, then the PVARP is immediately started and the sequence resumes at that point. Whatever was occurring at the time of the V-sense is immediately terminated.

(iii) If an A-sense occurs during the API, the remainder of the API is timed, the Alert and A-pace states are by-passed, and the AV delay is started at the end of the API, resulting in a prolonged AV delay (extended by that part of the API after the A-sense).

(iv) If an A-sense occurs during the Alert, the A-pace state is bypassed and the AV delay is started.

(v) If an A-sense occurs in the PVARP, it is counted in the rate averaging and starts an API. This will be the response when the atrial average rate is faster than the MIR rate.

(vi) If an A-sense occurs at any time other than during the PVARP, API and Alert states it is ignored and has no effect on the state sequencing.

FIG. 6 illustrates the sequence of states as a time line so that only the four intervals are shown. The points where the A-pace and the V-pace occur are indicated in this diagram, but for clarity are omitted in further diagrams.

Figure 7:
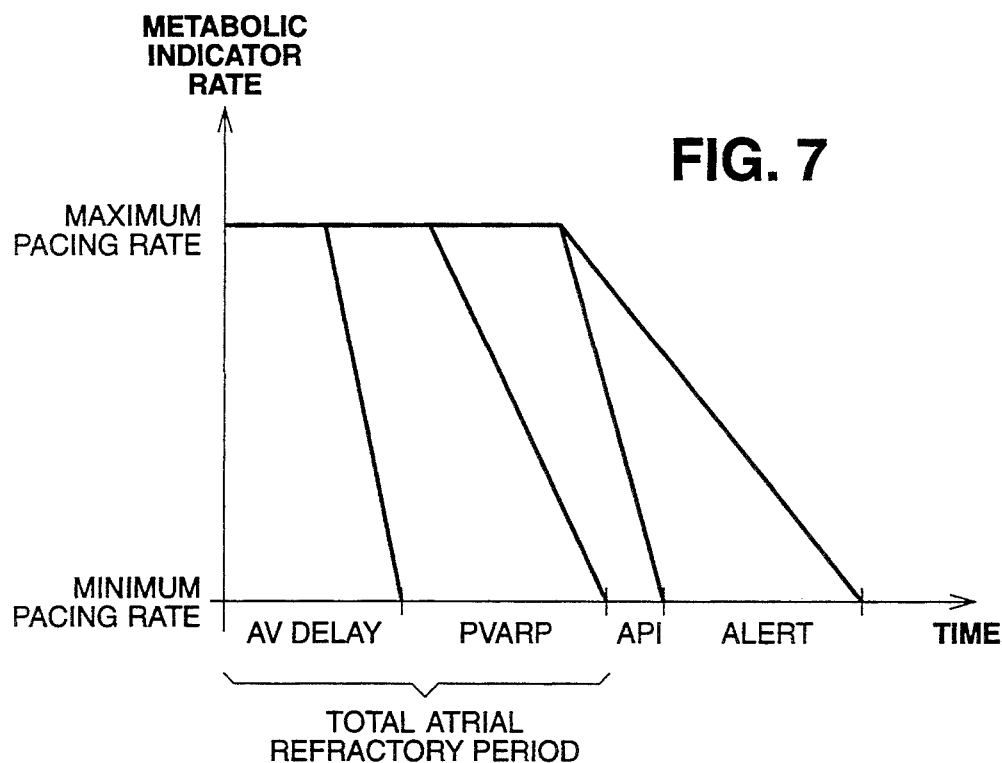
FIG. 7 is a timing diagram that shows the effect of a sensor-derived metabolic indicator rate.

The effect of the MIR is to modify each of these four intervals, as shown in FIG. 7. The four intervals are shown on the horizontal axis, similar to FIG. 6. The vertical axis is the MIR, ranging from the programmed minimum pacing rate to the programmed maximum pacing rate. There are five rules governing how the four intervals change with the MIR:

(i) The Alert interval is always greater than 0 ms at the minimum rate; otherwise the atrium cannot be tracked (i.e., if Alert equals 0 ms, DDDR pacing is not possible).

(ii) The Alert interval is always equal to 0 ms at the maximum rate. This means that the atrium cannot be tracked above the maximum pacing rate. Hence, the maximum MIR defines the maximum ventricular pacing (and tracking) rate.

(iii) The AV delay, following an event in Alert, may be either a fixed value throughout the range of MIR or shorten as MIR increases (in the case shown, with a slope of 1:16).

(iv) The PVARP can shorten but not lengthen as the MIR increases.

(v) There is an Atrial Non-Competition Rule which states that there must always be a minimum time between a non-tracked atrial sense (pathological A-sense) and an atrial pace. This is satisfied by ensuring that the Total Atrial Refractory Period (TARP equals AV delay plus PVARP) is less than or equal to 70% (in the illustration embodiment of the invention) of the total cycle length (the sum of the four intervals). This is achieved in part by the PVARP adapting (i.e., changing) as the MIR increases and decreases, and by appropriately setting (i.e., programming) the API. The rule places limits on the possible combinations of minimum rate, AV delay and PVARP.

The API is calculated by the external programmer using the values for the selected minimum and maximum rates, AV delay and "PVARP Base" (so-called because it is the PVARP at the minimum or base rate):

(a) The API at maximum rate is calculated to satisfy two relationships: (i) Maximum rate equals 60,000/(A-V delay plus PVARP plus API), and (ii) API must be at least 30% of the total cycle at maximum rate (60,000/Maximum rate) in order to satisfy the Non-Competition Rule. Since the AV delay is known for any rate, PVARP is reduced if necessary to lengthen the API to at least 30% of the total cycle.

(b) The API at minimum rate also is calculated to satisfy two relationships: (i) Minimum Rate equals 60,000/(AV delay plus PVARP plus API plus Alert), and (ii) AV delay plus PVARP plus API (at minimum rate) is greater than or equal to maximum rate interval. The result of these relationships is that the sum of AV delay plus PVARP plus API is either constant or it decreases as the MIR increases. This is because the sum of these intervals defines the ventricular tracking limit for all values of MIR, and the tracking limit (in rate) increases with MIR. Given the values for API at the minimum and maximum rates, there is a linear change between these two values over the range of MIR (i.e., minimum to maximum rate).

Figure 8:
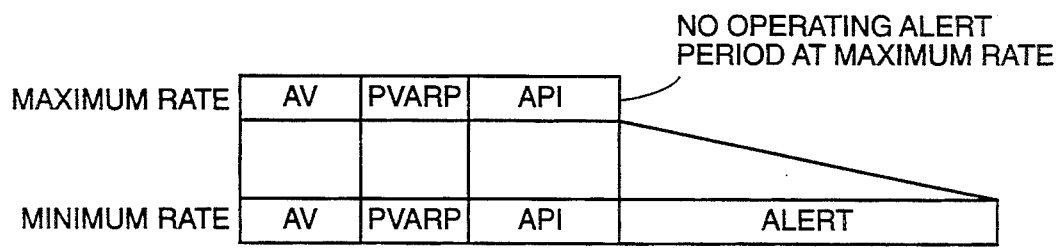
FIG. 8 is a line timing diagram showing the operating intervals for a short total atrial refractory period base.

The following examples illustrate a range of API values for different sets of programmed intervals (for clarity, a constant AV delay is used):

(i) FIG. 8: In this example, there is a relatively short value of PVARP, so that the Atrial Non-Competition Rule is not violated (i.e., TARP, which is the AV delay plus PVARP, is less than 70% of the pacing cycle for all values of MIR). Therefore, PVARP does not need to adapt (i.e., shorten) as the maximum rate is approached. By definition, Alert is 0 ms at maximum rate; therefore, API at maximum rate is calculated so that 60,000/maximum rate (the cycle duration) equals AV delay plus PVARP plus API. At minimum rate, the API is necessary so that the ventricular tracking limit (at minimum rate) at least equals the programmed maximum rate.

Figure 9:
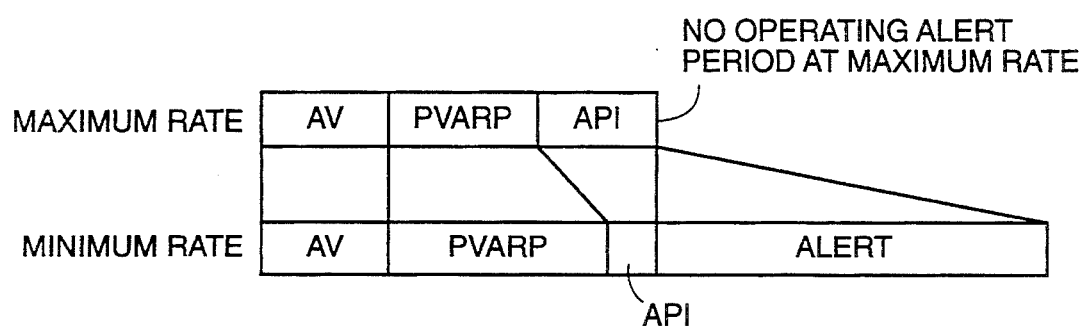
FIG. 9 is a line timing diagram showing the operating intervals for an intermediate total atrial refractory period base.

(ii) FIG. 9: Here a longer PVARP than the previous example has been selected so that it must adapt with MIR to satisfy the Atrial Non-Competition Rule. The API at maximum rate is calculated so that it equals 30% of 60,000/maximum rate. This relatively long API interval is at the expense of PVARP which shortens. As in the first example, the API at minimum rate results from the requirement that the ventricular tracking limit (at minimum rate) must at least equal (or be greater than) the programmed maximum rate.

Figure 10:
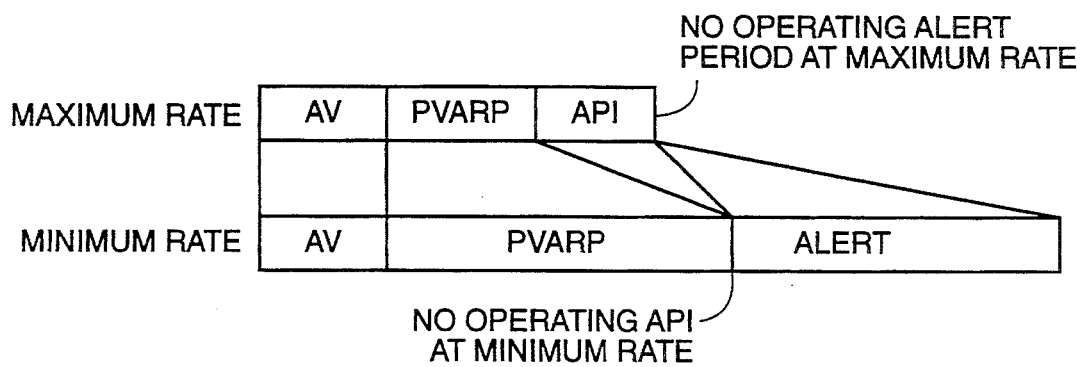
FIG. 10 is a line timing diagram showing the operating intervals for a long total atrial refractory period base.

(iii) FIG. 10: In this example, an even longer PVARP has been selected, but not too long since the Atrial Non Competition Rule is still satisfied. API at maximum rate is calculated in the same way as in the previous example. No API is required at the minimum rate because TARP at minimum rate is less than 70% of the total cycle time.

The purpose of the Automatic Mode Switching [AMS] function is to detect a nonphysiological atrial rate and rhythm and to thereupon automatically switch to a ventricular pacing mode, where atrial pacing is temporarily disabled and atrial sensed events are not tracked in the ventricular channel. If the pacemaker is operating in a VDD or DDD mode, then it will shift to VVI at the programmed standby rate. If the pacemaker is operating in a VDDR or DDDR mode, then it will shift to VVIR at the metabolic indicated rate. This switching function is controlled by the Atrial Rate Monitor [ARM] which must be programmed for a threshold heartbeat high rate and the number (count) of heartbeats at or above that high rate. In an exemplary ARM, the possible rates are 150, 175 or 200 beats per minute; and the possible counts are 5 or 11 beats.

The ARM 53B is shown as a block in FIG. 4 and as a logic diagram in FIG. 11. The ARM measures intervals between atrial events, whether paced or sensed or both. It monitors and counts as "long" intervals those which are longer than the interval of the programmed AMS rate, and as "short" intervals those which are shorter than the interval of the programmed AMS rate.

The Interval Measure 53B1 operates on the externally programmed AMS Rate (150, 175 or 200 beats per minute) from the Internal Bus 40, and the A-sense 45 and the A-pace 46 controls. There are two counters 53B2 and 53B3 which are incremented (+1) or decremented (−1) depending on the length of the measured interval and the programmed AMS rate. Only one counter is activated at a time. If AMS is not in effect, the short interval counter 53B2 is activated. This counter is incremented when a short interval is measured (i.e., the atrial rate is above the AMS Rate) and decremented when a long interval is measured. When the short interval counter reaches a certain limit (externally programmable to 5 or 11 counts), then a high atrial rate has been detected, the AMS control is activated, and the mode is switched to inhibit atrial tracking.

When the Automatic Mode Switching [AMS] control becomes operational, the short interval counter 53B2 is cleared (set to zero) and the long interval counter 53B3 is activated. This counter is incremented when a long interval is measured (i.e., the rate is below the AMS rate) and decremented when a short interval is measured. When it reaches 3 (not programmable in this implementation), the AMS control is deactivated. The AMS control will also be deactivated if the measured interval exceeds one second.

When the AMS control is deactivated, the mode is returned to atrial tracking, the short interval counter is activated, and the long interval counter is cleared.

The pacemaker described above is improved by the addition of the Forced Synchrony Function which overcomes the limitations of the conventional upper rate responses, namely, loss of AV synchrony and erratic VV intervals. The Forced Synchrony Function modifies the state sequence logic diagram of FIG. 5 as shown in the logic diagrams of FIGS. 12, 13, 14, and 15.

The principal purpose of Forced Synchrony is to ensure that an atrial event, either a P-wave or an A-pace, always precedes each V-pace, and that all AV delay intervals are within a defined range, controlled by the average V—V interval.

Figure 12:
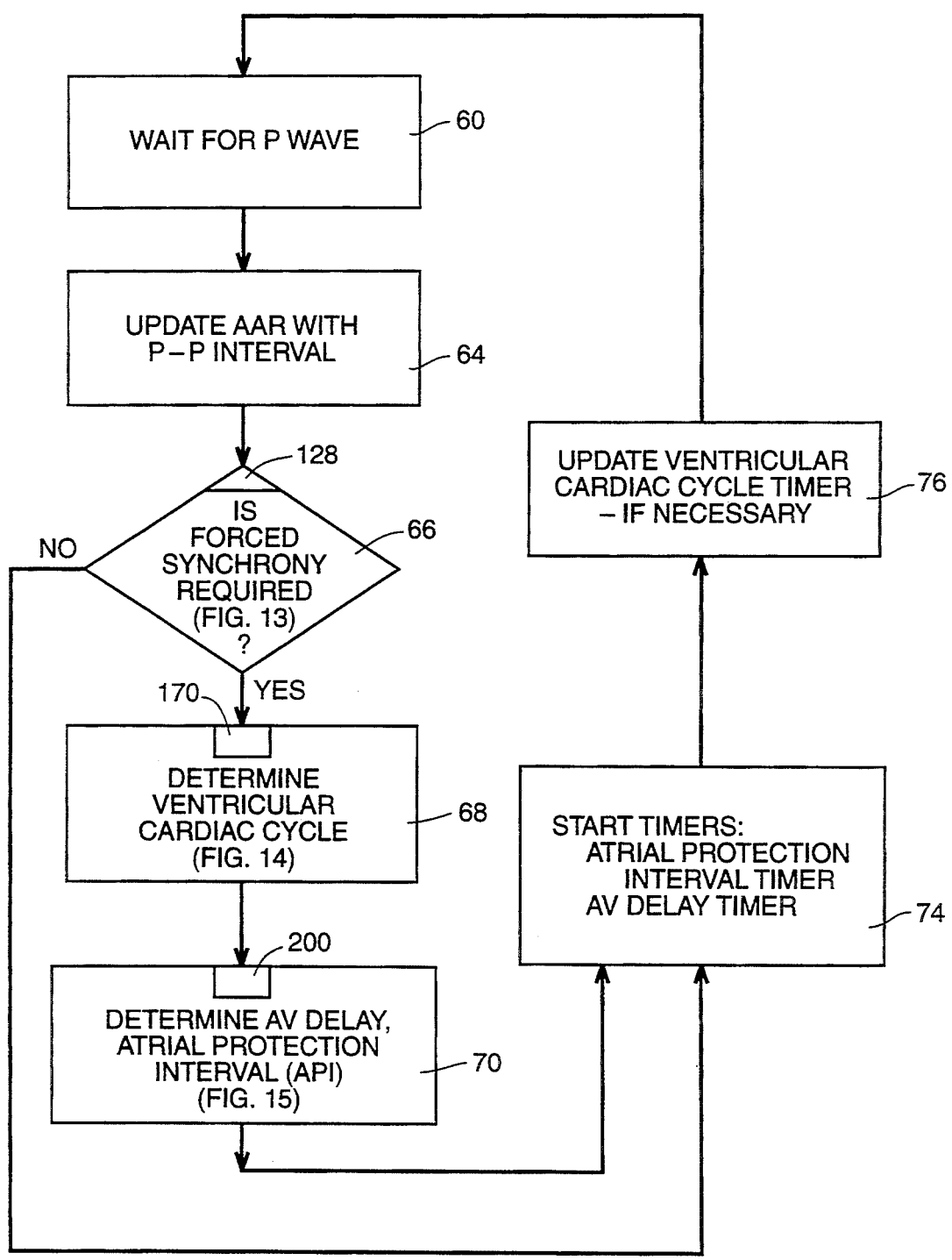
FIGS. 12, 13, 14 and 15 are logic diagrams illustrating operations performed by the pacemaker of FIG. 1 as it responds to a P-wave atrial depolarization.

FIG. 12 shows the logic of the Forced Synchrony control. Block 66 is shown in greater detail in FIG. 13 (in which block 128 is start), block 68 is shown in greater detail in FIG. 14 (in which block 170 is start), and block 70 is shown in greater detail in FIG. 15 (in which block 200 is start). The functions represented by all of these blocks are executed under software control by the microprocessor 19. The Atrial Protection Interval and the AV delay are no longer directly controlled by the Metabolic Indicator Rate. Rather, they are determined by the Forced Synchrony Control of FIG. 12 on a cardiac cycle by cycle basis. Further, when Forced Synchrony is in effect, the Alert interval is set to 0 ms for that particular cycle, i.e., A-senses are not tracked.

The Average Atrial Rate [AAR] is the reciprocal of the average P-wave to P-wave interval taken over a number of cycles, e.g., four cycles. The number is programmed by the physician. Thus the AAR monitors all atrial events, both P-wave and A-pace, over a number of cycles, and is continuously updated regardless of the particular mode of operation of the pacemaker.

Atrial senses occurring outside the Alert interval will not trigger the AMS until the rate and count criteria are met, but since they are above the ventricular maximum rate they are treated in a special manner. As described above, when the AMS rate and count criteria are met, this generally indicates an atrial arrhythmia and AMS will then cause a switchover in modes to VVIR.

Therefore, Forced Synchrony applies to sensed atrial events that are either not at a high enough rate or not consistent enough to cause AMS.

Figure 13:
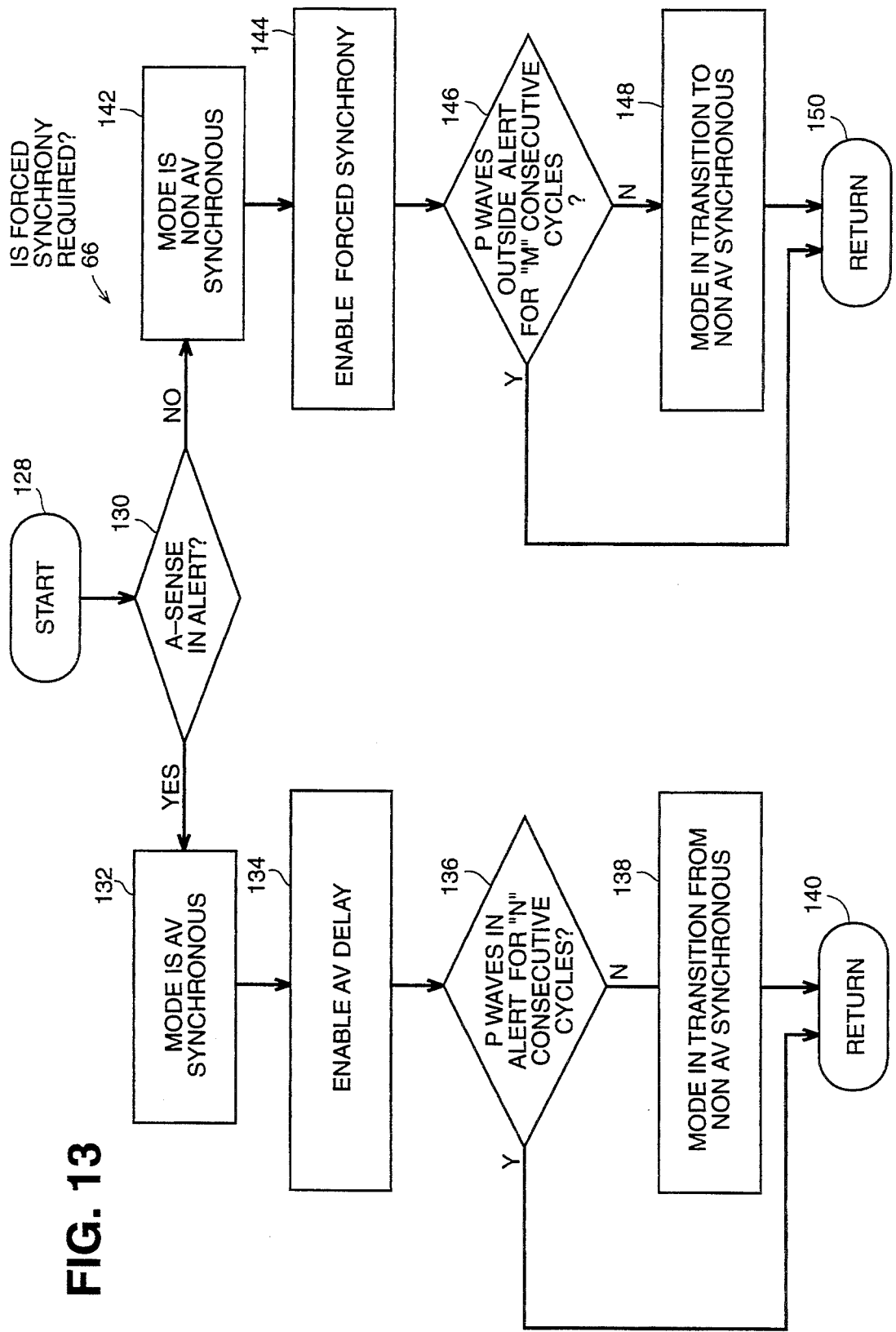
Figure 14:
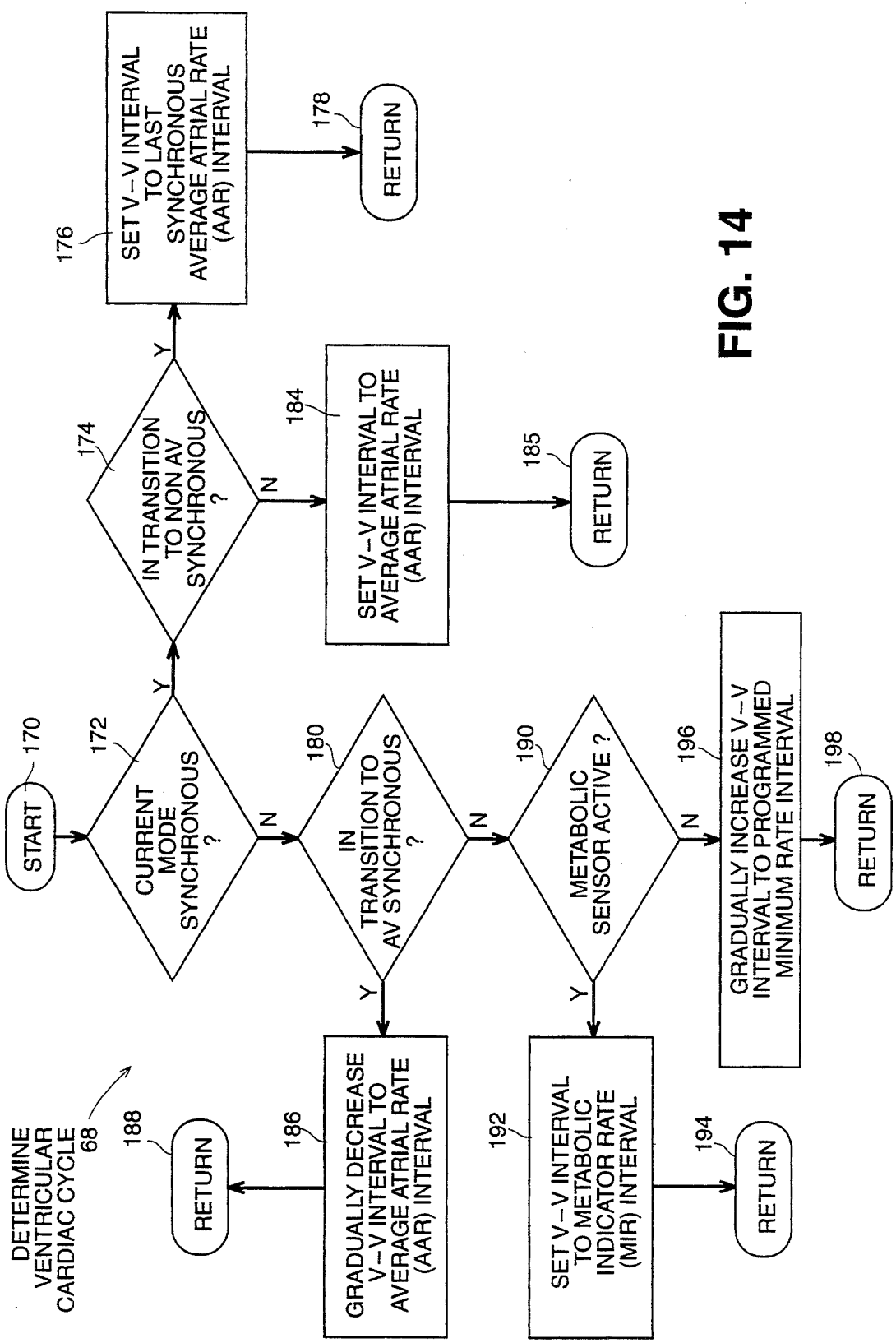

Whenever an atrial event is sensed in block 60, the AAR is updated in step 64; then its timing is checked in block 66 to determine if Forced Synchrony is required. The details of block 66 involved in this checking are shown in FIG. 13:

(i) If in block 130 it is determined that the A-sense occurred during the Alert Interval, then it must have been a P-wave. At block 132 the mode is set to synchronous, at block 134 the AV delay is initiated, and there is no Forced Synchrony Function; the rest of the pacer timing proceeds as described above for the normal state sequence of FIG. 5. In this case, the logic flow shown in FIG. 12 bypasses the block 68 for the determination of the VV interval and the block 70 for the calculation of the API and the AV delay. However, in block 136 in FIG. 13, the number of consecutive P-waves which occurred in the Alert Interval are compared to a limit ("N" which is programmable) to determine if there was recent non-AV synchronous operation. This information is used later to determine the VV interval. If there have not been P-waves in the Alert Intervals of N (e.g., three) consecutive cycles, then it is an indication that synchronous operation has only just started, i.e., a transition from non-synchronous to synchronous is in progress.

(ii) If the A-sense did not occur during the Alert Interval, as determined in block 130, then there may be an atrial arrhythmia occurring. The mode is set to non-AV synchronous in block 142, and Forced Synchrony operation is enabled. This means that the values of the API and AV delay will be recalculated to conform to the Forced Synchrony rules which are set out below. A check is also made in block 146 to determine if the A-senses have been consistently occurring outside the Alert Interval; if not, a transition from synchronous to non-synchronous operation may be in progress. This information is used later to determine the VV interval. The number of consecutive cycles "M" is programmable, and typically M=8.

To maintain stable VV intervals, the most appropriate rate information should be used. Block 68 of FIG. 12 is shown in detail in FIG. 14—the logic used in Forced Synchrony to decide from which of three sources, based on the current mode as determined in the previous processing (FIG. 13), the VV interval is determined. The three sources are the AAR, the MIR and the programmed minimum rate. To avoid sudden changes in the ventricular rate, there are cases where the VV interval is made to change smoothly from one of these sources to another. This occurs when the mode is in transition from or to an AV synchronous mode as previously determined in blocks 138 and 148 in FIG. 13.

If the current mode is AV synchronous, as determined in block 172, and in block 174 it is determined that a transition is not in progress, then the VV interval is set to the AAR in block 184. This is the usual routine operation if there are P-waves occurring in the Alert Interval and there have been no atrial arrhythmias in the last N cycles.

But if the current mode is AV synchronous and an A-sense has occurred outside the Alert interval, then the heart is in transition (this is potentially the start of an arrhythmia). In block 176, the VV interval is set to the last value of AAR that was AV synchronous, i.e., the last value of AAR before P-waves outside the Alert interval were detected.

But if the current mode is not AV synchronous, then either an arrhythmia is present or it has just terminated. In the first case, the test in block 180 is answered in the negative. If the MIR is determined to be active in block 190, the MIR is used to determine the rate in block 192. If the MIR is not active, then the VV interval is changed gradually in block 196 to the programmed minimum rate. (The gradual decrease and increase in V—V intervals in blocks 186 and 196 is typically 5 beats per minute per cycle.) This latter case is for pacemakers either without a sensor or where the sensor has been programmed off. Once the VV interval equals the minimum rate, it remains at that value until the arrhythmia terminates.

Once an arrhythmia terminates, and it is determined in step 180 that the mode is in transition to AV synchronous, then the VV interval is gradually changed in block 186 during successive cycles so that it becomes equal to the AAR.

Figure 15:
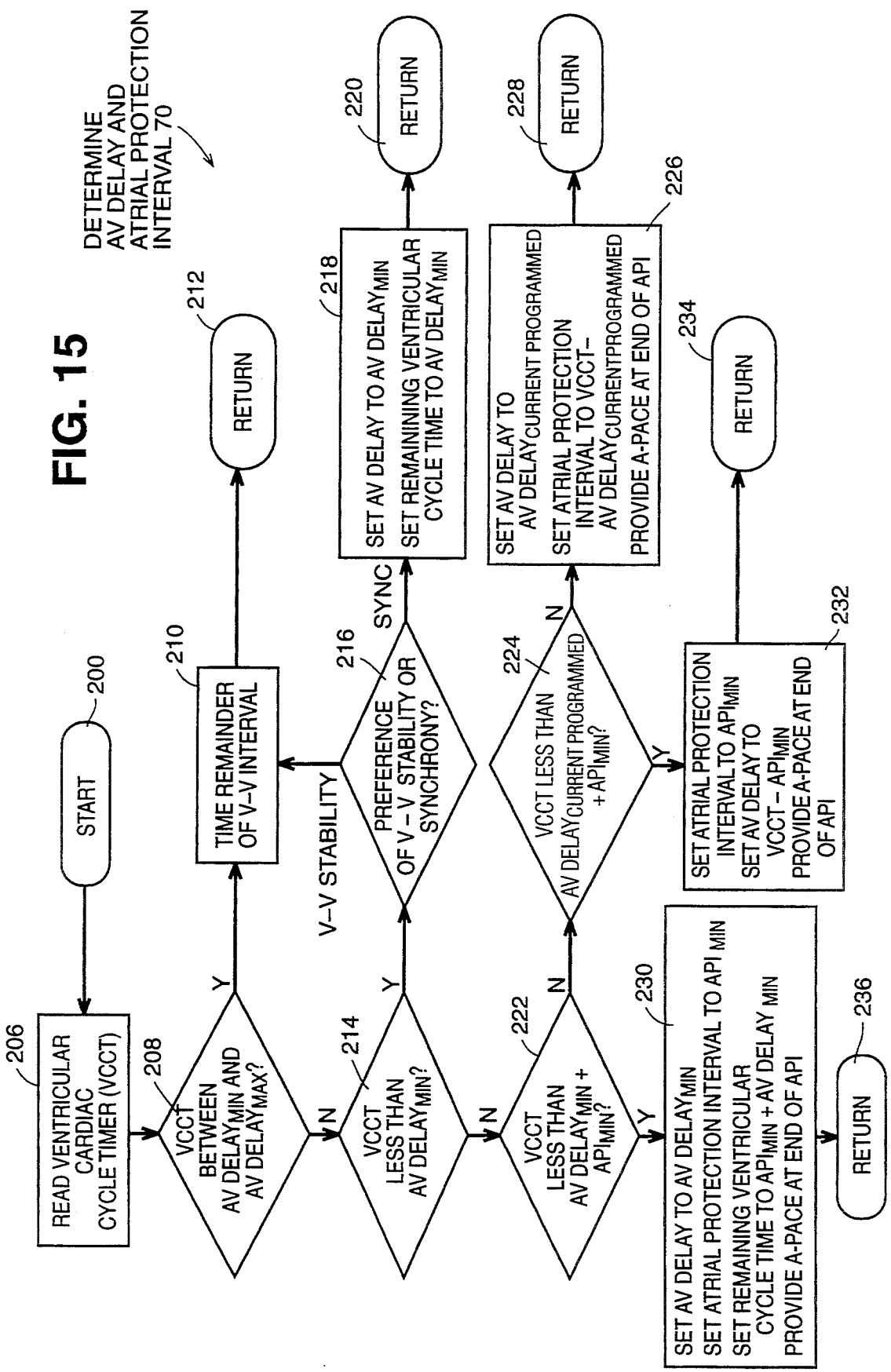

Referring to the Forced Synchrony Control of FIG. 12, once the VV interval is determined in block 68 (see FIG. 14) the API and the AV delay intervals are calculated. The logic for determining these intervals is shown in FIG. 15. The Ventricular Cardiac Cycle Timer [VCCT] value was initially set to the last VV interval, and it was decremented continuously during the current cycle until the P-wave under consideration was sensed. The remaining time in the VV cycle, i.e., the present value of VCCT, is obtained in block 206. This is the time remaining in the current VV interval, between the A-sense in block 60 of FIG. 12 and the time when the next V-pace is due, unless inhibited by the occurrence of an intrinsic R-wave. If the VCCT value is within the allowable range for the AV delay, determined in block 208, then the remainder of the VV interval is timed in block 210. This way, the VV interval need not change. A ventricular pace thus occurs at the desired rate, and it is preceded by an AV delay which is in a physiological range.

On the other hand, if the VCCT is determined in blocks 208 and 214 to be less than the minimum AV delay, then it is not possible to have both a physiologic AV delay and the desired VV interval—there is not enough time left in VCCT (at the end of which a V-pace will be generated) to allow even the minimum AV delay. The action is determined by whether AV synchrony or VV interval stability is preferred. (This may be a programmable option.) If VV interval stability is preferred, a branch is taken from block 216 to block 210—VCCT is not changed and the remainder of the VV interval is timed before a V-pace is generated. If AV synchrony is preferred, the minimum AV delay is timed and VCCT is set to this value in block 218. (The minimum value of the AV delay is used so as to change the VV interval by as little as possible.)

If block 222 is reached, then the VCCT (i.e., the prospective time from the A-sense just detected to the V-pace) must be greater than the maximum AV delay. Here Forced Synchrony enters the picture. The value of VCCT indicates that there is still part of the API and all of the AV delay yet to expire before a V-pace is to be generated. If all of this time goes by with no A-pace, the time interval between the P-wave just detected and the V-pace to be generated will be longer than the maximum AV delay. For physiologic pacing, an A-pace is desired. But if it is too close to the P-wave just detected, then the Non-Competition Rule will be violated—there must be a minimum API between any P-wave (actually sensed, or not sensed) and an A-pace. For this reason, an A-pace is generated between the sensed P-wave and the V-pace which will be generated after the AV delay. The A-pace is generated at a time which allows for a new API of at least minimum duration, and a physiologic AV delay. After the API is timed, an A-pace will be provided which will make the atrium and the AV node refractory. In general, this will block retrograde conduction of ventricular events. Since this A-pace is effectively the second atrial event for the VV cardiac cycle in progress, it is not used by the AAR and does not affect the logic of FIG. 12, i.e., it does not re-start the calculation process because that has already been done for this VV cardiac cycle. (Any other A-paces that occur at the end of the Alert interval are processed according to the logic in FIG. 12.)

If it is determined in block 222 that the Ventricular Cardiac Cycle Timer is not less than the sum of the minimum API and the minimum AV delay, i.e., there is a relatively long time left before a V-pace is due, the pacemaker attempts to use what is shown in FIG. 15 as the "current programmed" AV delay - the AV delay as determined by the MIR, or the AV delay as programmed for a non-sensor pacemaker. If the VCCT is not less than the current AV delay plus the minimum API, as determined in block 224, then the current AV delay is used, as shown in block 226. The remainder of the VCCT is used for the API, i.e., the API is made equal to the VCCT minus the current AV delay. In block 226, the need for an A-pace after the API is registered (the Forced Synchrony concept). If in block 224 it is determined that VCCT is less than the sum of the current AV delay and the minimum API, then there is not enough time left in the VCCT for both the minimum API and the current AV delay. The parameter values are set as shown in block 232, i.e., the API is set to its minimum value (the Non-Competition Rule must be satisfied), and the AV delay is set to the VCCT minus the minimum API. The overriding requirement is that the API must at least equal or be greater than the programmed minimum API value. In block 232, the need for an A-pace after the API interval is registered.

If at block 222 it is determined that the VCCT is less than the sum of the minimum API and the minimum AV delay, then the minimum values are used and the VV interval has to be extended as shown in block 230, i.e., the AV delay is set to the minimum AV delay, the API is set to the minimum API, and the VCCT is reset to the minimum API plus the minimum AV delay. There is no choice but to prolong the VV interval to the sum of the two minimum values. Again, the Forced Synchrony operation requires an A-pace at the end of the API to block possible retrograde conduction.

Figure 19:
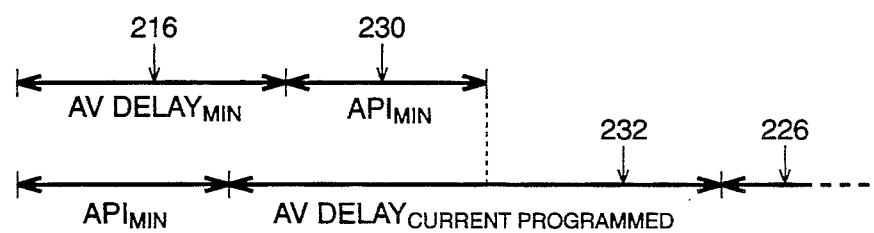
FIG. 19 depicts several time durations which will be helpful in understanding the logic diagram of FIG. 15.

The logic diagram of FIG. 15 is to some extent summarized by what is shown in FIG. 19. The intent here is to show several different VCCT ranges (the horizontal lines), A-senses occurring (the vertical arrows) when the remaining VCCT values are within these ranges, and which blocks (216, 226, 230 and 232) on FIG. 15 determine the new API and AV delay settings.

The upper left part of FIG. 19 depicts an A-sense occurring when VCCT is less than the minimum AV delay (determined in block 214 of FIG. 15). Since it is not possible to have both a physiologic AV delay and the desired VV interval in such a case (the desired VV interval would end with the end of AV delay timing, but the AV delay in such a case would be too short, i.e., less the minimum desired), a choice has to be made between VV stability and AV synchrony. This is done in logic block 216.

The upper horizontal line in FIG. 19 shows the minimum API following the minimum AV delay, but the drawing is not intended to show successive time intervals. Rather, the drawing depicts total VCCT values. The right half of the upper line depicts an A-sense occurring when VCCT is longer than the case just considered. The time remaining (VCCT) in the desired VV interval is longer than the minimum AV delay, but shorter than the sum of the minimum AV delay and the minimum API. Since an A-sense occurring when VCCT is less than the minimum AV delay results in logic block 216 on FIG. 15 being executed, the only way that logic block 222 on FIG. 15 can be reached is if an A-sense occurs when VCCT is longer then the minimum AV delay. If VCCT is shorter than the time limit of the test in block 222, then as shown in FIG. 19 block 230 is executed. The minimum values of AV delay and API are now set, and the VV interval is just a bit longer than desired. (The remaining time in the desired VV interval—VCCT—is measured from the left end of the upper horizontal line in FIG. 19 to the vertical arrow 230, and the extension of the VV interval is that part of the line to the right of the arrow.)

The first and second segments on the lower horizontal line of FIG. 19 add up to a longer time interval than that represented by the upper horizontal line because the current programmed AV delay is longer than the minimum AV delay. If VCCT is greater than the sum of the minimum AV delay and the minimum API (to the right of the upper horizontal line), determined by a negative answer to the question in block 222 of FIG. 15, but less than the sum of the minimum API and the current programmed AV delay, determined by a yes answer to the question in block 224, then block 232 is executed—as shown by arrow 232 in FIG. 19. The API is set to the minimum so that, when the remaining VV interval (the current value of VCCT) is timed, the AV delay will be as long as possible (although slightly less than the current programmed value).

Finally, if the answer to the question in block 224 is no, i.e., VCCT is longer than the sum of the minimum API and the current programmed AV delay, then, as shown by arrow 226 in FIG. 19, block 226 in FIG. 15 is executed. The current programmed AV delay is now used, and the API is set to the balance of the VCCT (a value longer than the minimum API).

After the values of API and AV delay are calculated, the cycle continues by starting the API timer and then the AV delay timer in block 74 of FIG. 12. If the VV interval had to be extended, the VCCF value is updated in block 76.

Figure 16:
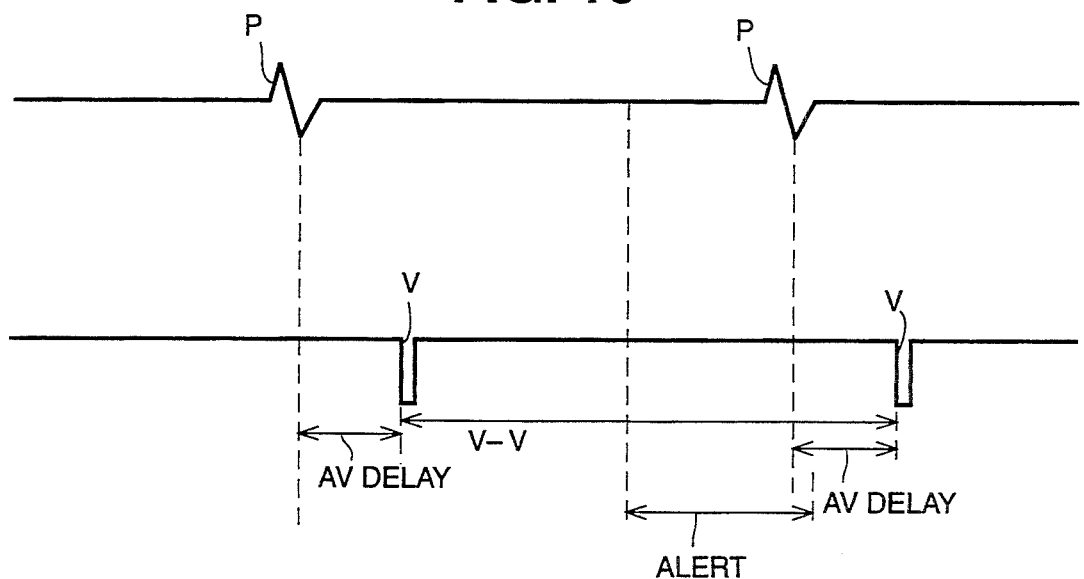
FIG. 16 is a timing diagram for two cardiac cycles illustrating the operation of the pacemaker of FIG. 1 in response to natural atrial depolarizations at a non-arrhythmia rate.
Figure 17:
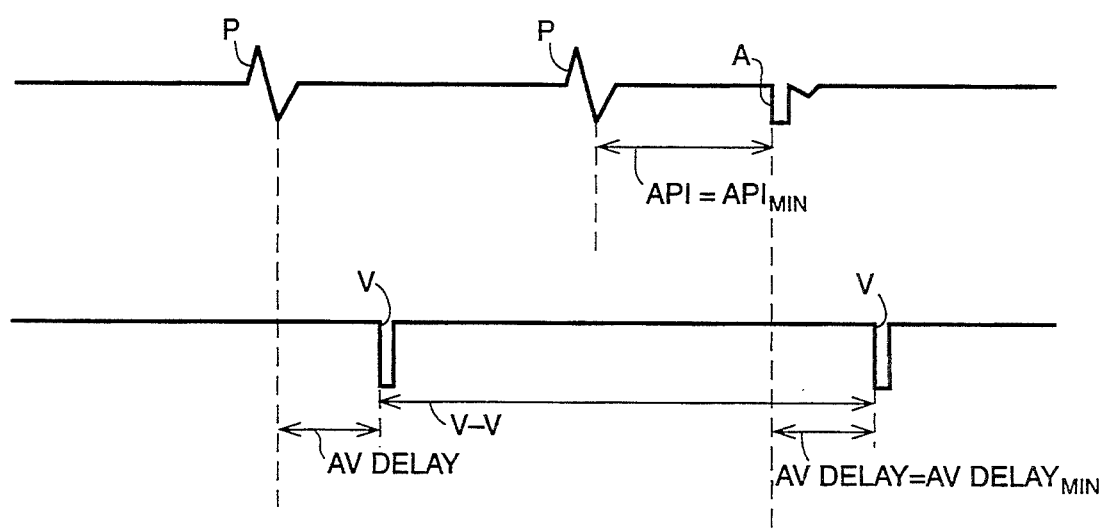
FIGS. 17 and 18 are timing diagrams for two heartbeat cycles illustrating the operation of the pacemaker of Fig. I in response to natural atrial depolarizations at an arrhythmia rate.
Figure 18:
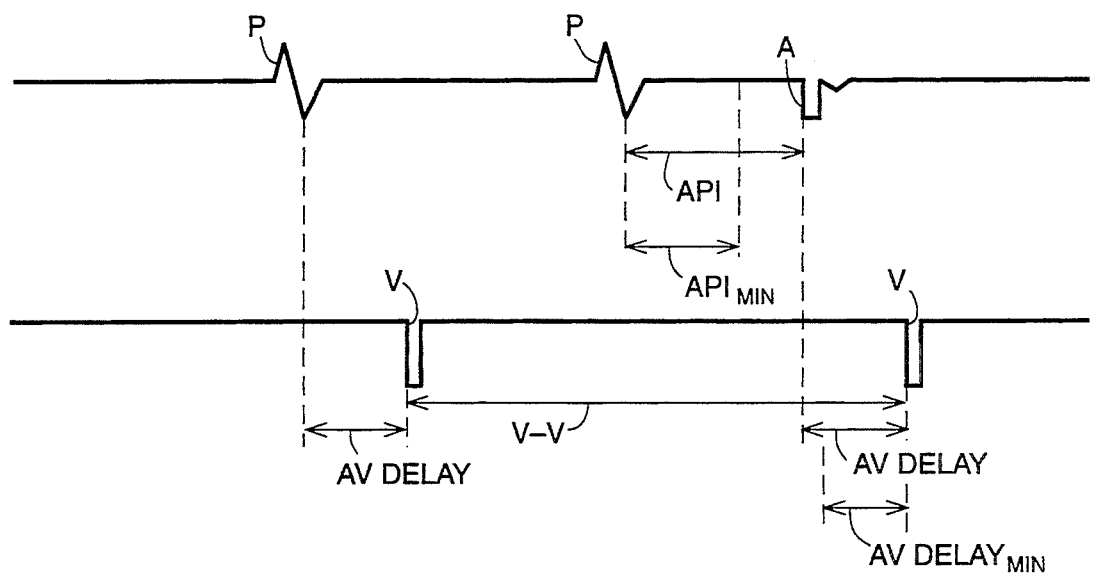

FIGS. 16, 17 and 18 illustrate the cyclings with tracked and early P-waves. FIG. 16 illustrates ventricular tracking of a P-wave occurring in the Alert interval. FIG. 17 shows an atrial event just before the Alert interval begins, where the VCCT is longer than the maximum AV delay but less than the sum of the minimum API plus the minimum AV delay. The minimum API is timed and then a Forced Synchrony A-pace is generated. The minimum AV delay follows the A-pace, after which a V-pace is generated. (See FIG. 15, block 230.)

FIG. 18 illustrates an atrial event even earlier than that of FIG. 17. Here an API longer than the minimum value of API is used, and then an A-pace is generated. The AV delay is the current value. (See FIG. 15, block 226.)

From the foregoing discussion, it is apparent that the pacemaker of the present invention greatly improves the upper rate response of a dual chamber cardiac pacemaker by providing forced synchrony cardiac pacing, thereby maintaining AV synchrony and improved hemodynamic behavior over a wider range of heart conditions. The stimulator of the present invention does not allow pacing with nonphysiological AV delay intervals which could otherwise provoke pacemaker mediated tachycardias.

Although the invention has been described with reference to particular embodiments, it is to be understood that these embodiment are merely illustrative of the application of the principles of the invention. Accordingly, the embodiment described in particular should be considered exemplary, not limiting, with respect to the following claims.

What is claimed is:

1. A dual-chamber pacemaker comprising:
   means for sensing an atrial heartbeat (A-sense);
   means for sensing a ventricular heartbeat (V-sense);
   means for generating an atrial pacing pulse (A-pace);
   means for generating a ventricular pacing pulse (V-pace);
   timer means for timing
   (i) a ventricular event to ventricular event interval (VV), such VV interval beginning with either a V-sense or a V-pace,
   (ii) an atrial event to V-pace interval (AV delay), such AV delay interval beginning with either an A-sense or an A-pace,
   (iii) an atrial protection interval (API),
   (iv) a post ventricular atrial refractory period (PVARP), and
   (v) an Alert interval (Alert); and
   controller means for providing a normal loop timing sequence of AV delay, PVARP, API, and Alert, with minimum time values for AV delay and API, and a maximum time value for AV delay; said controller means operating such that if an A-sense occurs during said API or PVARP and the remaining time in the VV interval is longer than said maximum AV delay, then an API is timed, at the end thereof an Apace is generated, and thereafter an appropriate AV delay is timed so as to stabilize the VV interval.

2. A dual-chamber pacemaker according to claim 1 wherein said controller means operates such that if the remaining time in the VV interval is shorter than the sum of the minimum API and the minimum AV delay, then a minimum API is timed, at the end thereof an A-pace is generated, and thereafter a minimum AV delay is timed.

3. A dual-chamber pacemaker according to claim 1 further including means for determining a desired AV delay (current AV delay), and wherein said controller means operates such that if the remaining time in the VV interval is longer than the sum of the current AV delay and said minimum API, then an API equal to the remaining time in the VV interval minus the current AV delay is timed, at the end thereof an A-pace is generated, and thereafter an AV delay equal to the current AV delay is timed.

4. A dual-chamber pacemaker according to claim 1 further including means for determining a desired AV delay (current AV delay), and wherein said controller means operates such that if the remaining time in the VV interval is shorter than the sum of the minimum API and the current AV delay but longer than the sum of the minimum API and the minimum AV delay, then a minimum API is timed, at the end thereof an A-pace is generated, and thereafter an AV delay equal to the remaining time in the VV interval minus the minimum API is timed.

5. A dual-chamber pacemaker according to claim 1 wherein said controller means operates such that if the time remaining in the VV interval is less than the minimum AV delay and AV synchrony is preferred over VV stability, then an AV delay equal to the minimum AV delay is timed to complete the VV interval.

6. A dual-chamber pacemaker according to claim 1 wherein said controller means operates such that if the remaining time in the VV intervals is less than the minimum AV delay and VV stability is preferred over AV synchrony, then the time remaining in the VV interval is timed to complete the VV interval.

7. A dual-chamber pacemaker according to claims 1, 2, 3, 4, 5 or 6 wherein said controller means determines whether the current mode of operation is AV synchronous, non-AV synchronous, or in transition between one of said modes to the other, and in each normal loop timing sequence said VV interval is set to a value dependent on the current mode.

8. A dual-chamber pacemaker according to claim 7 further including means for determining the average atrial rate and means for determining a minimum VV interval, and wherein said controller means operates such that (i) if the current mode is in transition from AV synchronous to non-AV synchronous, then the VV interval is set in accordance with the average atrial rate during the last synchronous mode, (ii) if the current mode is AV synchronous, then the VV interval is set in accordance with the average atrial rate, (iii) if the current mode is in transition from non-AV synchronous to AV synchronous, then the VV interval is gradually decreased over a number of cycles to correspond with the average atrial rate, and (iv) if the current mode is non-AV synchronous, then the VV interval is gradually increased over a number of cycles to correspond with the maximum VV interval.

9. A dual-chamber pacemaker according to claim 7 further including rate responsive sensor means and wherein said controller means sets said VV interval as a function of the operation of said rate responsive sensor means.

10. A dual-chamber pacemaker comprising:
means for sensing an atrial heartbeat (A-sense);
means for sensing a ventricular heartbeat (V-sense);
means for generating an atrial pacing pulse (A-pace);
means for generating a ventricular pacing pulse (V-pace);
timer means for timing
(i) an atrial event to V-pace interval (AV delay), such AV delay interval bet;inning with either an A-sense or an A-pace,
(ii) an atrial protection interval (API),
(iii) a post ventricular atrial refractory period (PVARP), and
(iv) an Alert interval (Alert); and
controller means for providing a normal loop timing sequence of AV delay, PVARP, API, and Alert; said controller means operating such that if an A-sense occurs during said API and the remaining time in the loop timing sequence is sufficient, then an API is timed, at the end thereof an A-pace is generated, and thereafter an AV delay is timed.

11. A dual-chamber pacemaker according to claim 10 wherein said controller means operates such that if said remaining time is relatively short, then a minimum API is timed, at the end thereof an A-pace is generated, and thereafter a minimum AV delay is timed.

12. A dual-chamber pacemaker according to claim 11 further including means for determining a desired AV delay (current AV delay), and wherein said controller means operates such that if said remaining time is relatively long, then an API equal to said remaining time minus the current AV delay is timed, at the end thereof an A-pace is generated, and thereafter an AV delay equal to the current AV delay is timed.

13. A dual-chamber pacemaker according to claim 12 wherein said controller means operates such that if said remaining time is in an intermediate range, then a minimum API is timed, at the end thereof an A-pace is generated, and thereafter an AV delay equal to said remaining time in the VV interval minus the minimum API is timed.

14. A dual-chamber pacemaker according to claim 13 wherein said controller means operates such that if said remaining time is very short and AV synchrony is preferred over VV stability, then an AV delay equal to the minimum AV delay is timed to complete the loop timing sequence.

15. A dual-chamber pacemaker according to claim 13 wherein said controller means operates such that if said remaining time is very short and VV stability is preferred over AV synchrony, then ..;aid remaining time is timed to complete the loop timing sequence.

16. A dual-chamber pacemaker according to claim 10 wherein said controller means operates such that if said remaining time is very short and AV synchrony is preferred over VV stability, then an AV delay equal to the minimum AV delay is timed to complete the loop timing sequence.

17. A dual-chamber pacemaker according to claim 16 wherein said controller means operates such that if said remaining time is very short and VV stability is preferred over AV synchrony, then said remaining time is timed to complete the loop timing sequence.

18. A dual-chamber pacemaker according to claims 10, 11, 12, 13, 14, 15, 16 or 17 wherein said controller means determines whether the current mode of operation is AV synchronous, non-AV synchronous, or in transition between one of said modes to the other, and in each normal loop timing sequence the loop time is set to a value dependent on the current mode.

19. A dual-chamber pacemaker according to claim 18 further including means for determining the average atrial rate and means for determining a minimum loop time, and wherein said controller means operates such that (i) if the current mode is in transition from AV synchronous to non-AV synchronous, then the loop time is set in accordance with the average atrial rate during the last synchronous mode, (ii) if the current mode is AV synchronous, then the loop time is set in accordance with the average atrial rate, (iii) if the current mode is in transition from non-AV synchronous to AV synchronous, then the loop time is gradually decreased over a number of cycles to correspond with the average atrial rate, and (iv) if the current mode is non-AV synchronous, then the loop time is gradually increased over a number of cycles to correspond with the maximum loop time.

20. A dual-chamber pacemaker according to claim 18 further including rate responsive sensor means and wherein said controller means sets said loop time as a function of the operation of said rate responsive sensor means when the current mode is non-AV synchronous.

21. A method of operating a dual-chamber pacemaker comprising the steps of:
sensing an atrial heartbeat (A-sense);
sensing a ventricular heartbeat (V-sense);
generating an atrial pacing pulse (A-pace);
generating a ventricular pacing pulse (V-pace);
timing
(i) a ventricular event to ventricular event interval (VV), such VV interval beginning with either a V-sense or a V-pace,
(ii) an atrial event to V-pace interval (AV delay), such AV delay interval beginning with either an A-sense or an A-pace,
(iii) an atrial protection interval (API),
(iv) a post ventricular atrial refractory period (PVARP), and
(v) an Alert interval (Alert); and
providing a normal loop timing sequence of AV delay, PVARP, API, and Alert, with minimum time values for AV delay and API, and a maximum time value for AV delay; wherein if an A-sense occurs prior to the Alert interval and the remaining time in the VV interval is longer than said maximum AV delay, then an API is timed, at the end thereof an A-pace is generated, and thereafter an AV delay is timed.

22. A method of operating a dual-chamber pacemaker according to claim 21 wherein if the remaining time in the VV interval is shorter than the sum of the minimum API and the minimum AV delay, then a minimum API is timed, at the end thereof an A-pace is generated, and thereafter a minimum AV delay is timed.

23. A method of operating a dual-chamber pacemaker according to claim 21 further including the step of determining a desired AV delay (current AV delay), and wherein if the remaining time in the VV interval is longer than the sum of the current AV delay and said minimum API, then an API equal to the remaining time in the VV interval minus the current AV delay is timed, at the end thereof an A-pace is generated, and thereafter an AV delay equal to the current AV delay is timed.

24. A method of operating a dual-chamber pacemaker according to claim 21 further including the step of determining a desired AV delay (current AV delay), and wherein if the remaining time in the VV interval is shorter than the sum of the minimum API and the current AV delay but longer than the sum of the minimum API and the minimum AV delay, then a minimum API is timed, at the end thereof an A-pace is generated, and thereafter an AV delay equal to the remaining time in the VV interval minus the minimum API is timed.

25. A method of operating a dual-chamber pacemaker according to claim 21 wherein if the time remaining in the VV interval is less than the minimum AV delay and AV synchrony is preferred over VV stability, then an AV delay equal to the minimum AV delay is timed to complete the VV interval.

26. A method of operating a dual-chamber pacemaker according to claim 21 wherein if the remaining time in the VV interval is less than the minimum AV delay and VV stability is preferred over AV synchrony, then the time remaining in the VV interval is timed to complete the VV interval.

27. A method of operating a dual.-chamber pacemaker according to claims 21, 22, 23, 24, 25 or 26 further including the step of determining whether the current mode of operation is AV synchronous, non-AV synchronous, or in transition between one of said modes to the other, and in each normal loop timing sequence said VV interval is set to a value dependent on the current mode.

28. A method of operating a dual.-chamber pacemaker according to claim 27 further including the step of determining the average atrial rate and a minimum VV interval, and wherein (i) if the current mode is in transition from AV synchronous to non-AV synchronous, then the VV interval is set in accordance with the average atrial rate during the last synchronous mode, (ii) if the current mode is AV synchronous, then the VV interval is set in accordance with the average atrial rate, (iii) if the current mode is in transition from non-AV synchronous to AV synchronous, then the VV interval is gradually decreased over a number of cycles to correspond with the average atrial rate, and (iv) if the current mode is non-AV synchronous, then the VV interval is gradually increased over a number of cycles to correspond with the maximum VV interval.

29. A method of operating a dual-chamber pacemaker according to claim 27 further including the step of setting said VV interval as a function of the rate response of the pacemaker when the current mode is non-AV synchronous.

30. A method of operating a dual-chamber pacemaker comprising the steps of:
sensing an atrial heartbeat (A-sense);
sensing a ventricular heartbeat (V-sense);
generating an atrial pacing pulse (A-pace);
generating a ventricular pacing pulse (V-pace);
timing
(i) an atrial event to V-pace interval (AV delay), such AV delay interval beginning with either an A-sense or an A-pace,
(ii) an atrial protection interval (API),
(iii) a post ventricular atrial refractory period (PVARP), and
(iv) an Alert interval (Alert); and
providing a normal loop timing sequence of AV delay, PVARP, API, and Alert; wherein if an A-sense occurs prior to the Alert interval and the remaining time in the loop tinting sequence is sufficient, then an API is timed, at the end thereof an Apace is generated, and thereafter an AV delay is timed.

31. A method of operating a dual-chamber pacemaker according to claim 30 wherein if said remaining time is relatively short, then a minimum API is timed, at the end thereof an A-pace is generated, and thereafter a minimum AV delay is timed.

32. A method of operating a dual.-chamber pacemaker according to claim 31 further including the step of determining a desired AV delay (current AV delay), and wherein if said remaining time is relatively long, then an API equal to said remaining time minus the current AV delay is timed, at the end thereof an A-pace is generated, and thereafter an AV delay equal to the current AV delay is timed.

33. A method of operating a dual-chamber pacemaker according to claim 32 wherein if said remaining time is in an intermediate range, then a minimum API is timed, at the end thereof an A-pace is generated, and thereafter an AV delay equal to said remaining time minus the minimum API is timed.

34. A method of operating a dual-.chamber pacemaker according to claim 33 wherein if said remaining time is very short and AV synchrony is preferred over VV stability, then an AV delay equal to the minimum AV delay is timed to complete the loop timing sequence.

35. A method of operating a dual-chamber pacemaker according to claim 33 wherein if said remaining time is very short and VV stability is preferred over AV synchrony, then said remaining time is timed to complete the loop timing sequence.

36. A method of operating a dual-chamber pacemaker according to claim 30 wherein if said remaining time is very short and AV synchrony is preferred over VV stability, then an AV delay equal to the minimum AV delay is timed to complete the loop timing sequence.

37. A method of operating a dual-chamber pacemaker according to claim 36 wherein if said remaining time is very short and VV stability is preferred over AV synchrony, then said remaining time is timed to complete the loop timing sequence.

38. A method of operating a dual-chamber pacemaker according to claims 30, 31, 32, 33, 34, 35, 36 or 37 further including the step of determining whether the current mode of operation is AV synchronous, non-AV synchronous, or in transition between one of said modes to the other, and in each normal loop timing sequence the loop time is set to a value dependent on the current mode.

39. A method of operating a dual-chamber pacemaker according to claim 38 further including the step of determining the average atrial rate and a minimum loop time, and wherein (i) if the current mode is in transition from AV synchronous to non-AV synchronous, then the loop time is set in accordance with the average atrial rate during the last synchronous mode, (ii) if the current mode is AV synchronous, then the loop time is set in accordance with the average atrial rate, (iii) if the current mode is in transition from non-AV synchronous to AV synchronous, then the loop time is gradually decreased over a number of cycles to correspond with the average atrial rate, and (iv) if the current mode is non-AV synchronous, then the loop time is gradually increased over a number of cycles to correspond with the maximum loop time.

40. A method of operating a dual-chamber pacemaker according to claim 38 further including the step of setting said 10op time as a function of the rate response of the pacemaker when the current mode is non-AV synchronous.

* * * * *